United States Patent [19]

Beigler et al.

[11] 4,003,992
[45] Jan. 18, 1977

[54] HYDROLYTIC PROCESS FOR THE PREPARATION OF AMINO ACIDS

[75] Inventors: Myron A. Beigler, Palo Alto; William B. Benken, San Jose; Jorge J. Nassar, Sunnyvale, all of Calif.

[73] Assignee: Syntex (U.S.A.) Inc., Palo Alto, Calif.

[22] Filed: June 16, 1975

[21] Appl. No.: 587,016

[52] U.S. Cl. .............................. 424/101; 424/319
[51] Int. Cl.² ............... A61K 35/14; A61K 31/195
[58] Field of Search .......................... 424/101, 319

[56] References Cited

UNITED STATES PATENTS 3,579,495   5/1971   Huber ............................... 424/101

*Primary Examiner*—Sam Rosen
*Attorney, Agent, or Firm*—Alan M. Krubiner; William B. Walker

[57] ABSTRACT

A highly efficient process for preparing a nutritionally acceptable mixture of amino acids from erythrocytes comprises the steps of denaturization, hydrolysis and neutralization, desludging, decolorization, deionization, concentration and sterilization.

17 Claims, No Drawings

HYDROLYTIC PROCESS FOR THE PREPARATION OF AMINO ACIDS

BACKGROUND OF THE INVENTION

In recent years there has been widespread use of amino acid mixtures in nutritional compositions.

The use of such compositions for intravenous administration has become of particular importance.

In part, this is due to the recognition that amino acids help to maintain the proper nitrogen balance and necessary nutritional state of the body, serving as building blocks for body protein.

While there is voluminous literature describing both theoretical and practical approaches for obtaining free amino acid mixtures from whole protein by hydrolytic methods, (e.g., U.S. Pat. Nos. 2,241,927, 2,460,040, 2,555,276 and 2,991,309) few if any of these methods are being employed commercially because of the technical problems, lack of high quality, inexpensive protein sources and/or the inherent cost factors due to processing.

In particular, prior art hydrolytic processes leading to amino acid mixtures do not, with limited exceptions (see e.g., U.S. Pat. No. 2,680,744), concern themselves with the removal of nutritionally undesirable contaminants or by-products such as peptides, iron and other heavy metals, as well as ammonia.

Thus, it would be desirable to have available a highly efficient, relatively inexpensive process for preparing, from readily available protein sources, amino acid mixtures free from undesirable contaminants, suitable for use in nutritional compositions, and particularly suitable for intravenous administration.

BRIEF DESCRIPTION OF THE INVENTION

The process of the present invention involves the preparation of nutritionally acceptable amino acid mixtures by the hydrolysis of erythrocytes. The highly efficient, multi-step process may be performed on a commercial scale, in a batch or continuous manner, and, involves the following operations:
1. denaturization of the protein
2. acid hydrolysis followed by partial neutralization
3. desludging
4. decolorization
5. deionization
6. concentration, and
7. sterilization of the final amino acid mixture.

The amino acid mixture may be prepared either as a solution or in dried form useful for further processing.

DETAILED DESCRIPTION OF THE INVENTION

The present process is a multi-step procedure involving the hydrolysis of erythrocytes to afford a high quality, nutritionally acceptable, sterile amino acid mixture. As used in the present specification the term "nutritionally acceptable" means that the resultant amino acids are in the L-form preferred by the body for utilization in the biochemical and physiological processes necessary to achieve a healthy nutritional status and are free of peptides and toxic amino acid derivatives, as well as being substantially free of certain chemical ions, particularly iron and other heavy metal cations. Specifically, the iron content should be ≤ 30 ppm, the other heavy metal (Pb,Cu,Zn,Mn) content ≤ 10 ppm, chloride ≤ 0.02%, sulfate ≤ 0.03% and sodium ≤ 1.6%. In preferred embodiments the ammonia level is ≤ 0.02%. The substantial absence of iron and other heavy metal ions makes the amino acid mixture particularly useful for intravenous administration.

The major steps of the process are seven in number, and when combined as described below result in a highly efficient and relatively inexpensive process for the preparation of large quantities of amino acid mixture.

The protein source (i.e., starting material) for the present process is erythrocytes (i.e., red blood cells). Erythrocytes are obtained in large quantities as a by-product from animal slaughter and serum extraction operations and are generally discarded. A preferred starting material for the process is bovine erythrocytes.

The general nature of the process involves the hydrolysis of the erythrocytes, which are largely composed of the protein hemoglobin, to afford a crude mixture of amino acids, followed by purification of this crude hydrolysate involving the removal of various by-products from the hydrolysis (e.g., aromatic and heterocyclic heme breakdown products), deionization, removal of water to afford a more concentrated solution, and sterilization of the final product.

The first part of the process involves a pre-treatment of the erythrocytes so as to denature the protein (hemoglobin) and to remove various soluble salts, carbohydrates and lipids. Certain salts (e.g. sodium citrate and sodium chloride) are normally present as contaminants introduced during the earlier processing of the erythrocytes by serum extraction. Failure to remove these salts at this stage can complicate the later purification on the cation exchange column, requiring different operating parameters, larger columns, and so forth.

The pre-treatment step is preferably effected by means of heat, followed by a filtration and water wash. In a preferred embodiment, the heat source is steam which is introduced into a water suspension of the erythrocytes, causing destruction of the erythrocytes and irreversible denaturization of the protein. The insoluble protein is then separated from the soluble materials (salts, carbohydrates and lipids) by filtration and water wash.

The next step in the process is the acid hydrolysis of the denatured protein. This hydrolysis is carried out utilizing sulfuric acid at elevated temperature. The sulfuric acid used should be at least 6N and is preferably about 8N. The hydrolysis temperature should be greater than 200° F and preferably will be equal to or greater than 258° F.

It has been determined that when the hydrolysis is conducted utilizing 8N sulfuric acid at a temperature of 258° F or greater, for 6 hours or longer, peptide-free amino acid mixtures are obtained. This is particularly important since the presence of (unhydrolyzed) peptides in the final amino acid mixture can have detrimental effects, for example, by causing anaphylactic shock or other types of sensitivity when administered to certain subjects. In any event, the hydrolysis may be monitored to determine when the final mixture is peptide-free by analysis on an amino acid analyzer. The amino acid yields obtained after the above hydrolysis normally exceed 95% based on the weight of the original protein.

After the hydrolysis is complete the mixture is partially neutralized by addition of calcium hydroxide to a final pH of between about 2.7 and 3.5. This partial neutralization removes excess sulfuric acid while maintaining the amino acids formed in the protonated form.

This also is of importance in the later deionization step utilizing a cationic exchange column.

The neutralization with calcium hydroxide results in the formation of a calcium sulfate cake which also contains certain humin by-products of the hydrolysis. This calcium sulfate-humin cake is removed in a desludging step. The cake has a substantially higher specific gravity than the hydrolysate and therefore may be readily separated from the hydrolysate by various filtration techniques such as on a Buchner filter, by allowing the cake to settle and decanting the supernatent, by use of a plate and frame press or by use of a basket centrifugal. Other filtration techniques well known to those skilled in the art may also be utilized with satisfactory results.

In the next step essentially all of the remaining dark colored humin material is removed by decolorization. Decolorization techniques well known in the art may be utilized. A particularly preferred method is the use of activated charcoal involving the admixture of the charcoal with the hydrolysate, followed by filtration. Various ratios of charcoal to hydrolysate may be used, but a particularly preferred ratio is from about 1 to about 2% w/w of charcoal relative to hydrolysate. Such a treatment generally removes approximately 98% of the color from the hydrolysate as measured by colorimetry. Alternate decolorization techniques involve, for example, the passage of the hydrolysate through a strong cation exchange resin (of the type described, infra, for deionization) which removes approximately 95% of the color from the hydrolysate. Further passage through a weak anionic macro-reticular phenol-formaldehyde resin such as the Duolite S-37 resin, will remove additional color affording a final hydrolysate comparable to that obtained after charcoal treatment.

In the next step most of the nutritionally objectionable ions present in the hydrolysate are removed. In particular, nutritionally objectionable metal cations such as iron, zinc, copper, manganese and lead are removed or reduced to acceptable levels. Additionally, most of the anions, e.g., sulfate and chloride, are also removed. Thus, the final amino acid mixture is essentially free of nutritionally objectionable ions.

The deionization step involves the use of a strong cationic exchange resin comprising a sulfonated copolymer of styrene cross-linked with approximately 8% divinyl benzene. A preferred bead size is 40–80 mesh. A particularly preferred commercially available resin is the Duolite C-20 resin. The column is loaded by passing a solution of the amino acid hydrolysate onto the column. After loading, the column is washed sulfate-free with water and then the amino acids are eluted by passage of a dilute sodium hydroxide solution through the column. The use of sodium hydroxide solution of $\leq 0.1N$ is preferred to elute the amino acids. The amino acids are collected up until a desired pH of the eluate. Preferably, amino acids are collected up until a pH of about 12.0. In such a manner, it has been found that approximately 95% of the amino acids loaded on the column are recovered.

In the next step, the hydrolysate is concentrated by removal of between about 60 and 80% of the water. Concentration may be accomplished according to procedures well known in the art such as evaporation, flash distillation and the like. However, these all involve the use of relatively sophisticated and expensive equipment. It has been found that a particularly preferred method of concentration involves passage through an ion exchange column. A column similar or identical to that used in the previous step may be utilized for the concentration, thus reducing the need for additional equipment.

Prior to the concentration, the basic eluate from the previous step is acidified to about pH 3.0 with sulfuric acid and the acidified solution is then loaded on the column, washed sulfate free and then eluted with sodium hydroxide solution more concentrated than that utilized in the deionization step, e.g., with 0.5N sodium hydroxide. Due to the stoichiometric nature of the ion exchange column, the amino acids elute in a smaller volume than that in which they were applied to the column, thus affording a more concentrated solution. Additionally, the further passage through the ion exchange column serves to substantially remove any residual objectionable ions (e.g., iron) which might leak through the first column.

The amino acid solution obtained in the above step is next subjected to sterilization (i.e., freed of microbial contamination) prior to its use as a component of a nutritional formulation. Sterilization may be effected according to procedures known per se in the art such as for example by heating or by millipore filtration.

In particular preferred embodiments sterilization is effected concurrently with removal of residual volatile materials.

A common residual volatile material is ammonia produced during the hydrolysis, and is objectionable in many nutritional formulations. It has been found that by the use of a steam injection-flash evaporation technique, the solution may be sterilized and residual volatiles, notably ammonia, may be reduced to acceptable levels, in a single operation. Alternate procedures such as low temperature evaporation or millipore filtration do not reduce ammonia content. The technique for the steam injection and flash evaporation are those generally well known in the art, involving a relatively short (less than 1 minute) contact time with the steam, thereby avoiding destruction of the amino acids.

The final amino acid solution produced by the above steps is colorless and contains at least 2% w/w, and preferably between about 2 and about 4% w/w of amino acids, and has a pH between about 8.0 and 9.0. It has an iron content of $\leq 30$ ppm, a heavy metal content of $\leq 10$ ppm and ammonia levels of $\leq 0.02\%$. The solution itself may be aseptically packaged or may be spray dried to afford a mixture of crystalline amino acids for further use in nutritional preparations.

The process of the present invention is particularly suitable for large scale production, and the flexibility and simplicity of the equipment allows for either batch or continuous operation.

A detailed description of preferred embodiments of the present invention is presented in the examples below. However, it should be understood that the examples are non-limiting and are illustrative only of the invention. It is expected that many variations may be made on the processes illustrated in the examples without departing from the scope or spirit of the invention.

EXAMPLE 1

Pretreatment

One hundred pounds of bovine erythrocytes are combined with 400 pounds of water in a kettle and mixed with high shear agitation. Steam (20 psig) is injected directly into the erythrocyte slurry for 45 minutes to 1 hour. The heat denatured protein is pumped into a perforated basket centrifugal where the solubles are removed with the water. This is followed by cake washing with 100 pounds of water. This results in a semi-dry cake containing 30–40% total solids which may be further dried, if desired, for use in the hydrolysis step.

EXAMPLE 2

Acid Hydrolysis and Partial Neutralization

Twenty pounds of dry denatured erythrocyte solids and 60–80 pounds of 8N sulfuric acid are heated at 258° F or greater (16 psig) for six hours, not including 20 minute preheating time. The mixture is allowed to cool to 150° C and a 20% w/w calcium hydroxide slurry slowly added to a final pH of 2.7 to 3.5. After cooling the mixture is desludged as in the following example.

EXAMPLE 3

Desludging

A. The mixture from the above example is placed in a kettle and the heavy crystalline solids are allowed to settle. The supernatant (containing 1–5% fine solids) is decanted and is filtered using a plate and frame press equipped with cotton filter cloths. The solids in the press and those left in the kettle are exhaustively water washed. Typical recoveries vary between 85 and 95% depending upon the thoroughness of the wash step.

B. In an alternate procedure, the mixture from Example 3 is pumped into a basket centrifugal, and the solution containing the amino acids and soluble salts is separated from the calcium sulfate cake. This cake is washed with hot (140° F) water, and the washings combined with the above solution.

EXAMPLE 4

Decolorization

In a typical run 1.5 pounds of powdered charcoal are combined with 100 pounds hydrolysate in a kettle (approximately 5–6% amino acid solution w/v) and mixed for 30 minutes with a high shear agitator. The slurry is then filtered using a plate and frame press. The filtrate is examined by colorimetry indicating that 98% of the initial color has been removed. The filtrate is then used in the next step.

EXAMPLE 5

Deionization

The resin utilized for the column is Duolite C-20 (40–80 mesh bead size). The height:diameter ratio for the column is between about 4:1 and 8:1. The C-20 resin is stored in the sodium form (pH $\geq$ 12). Prior to loading, the resin is converted to the hydrogen form by passing four bed volumes of 1.5N sulfuric acid through the resin. After regeneration the resin is backwashed with water (4–5 bed volumes) and then is cocurrently rinsed with 2 bed volumes of water to compact the bed and prepare it for loading. The column is then loaded with erythrocyte hydrolysate (pH 3.5) by passing the hydrolysate through the column at a flow rate between about 1 and 5 gal/ft$^3$min. In such a manner, the resin binds between about 4 and 6 kg amino acids/ft$^3$min. After loading, the column is washed cocurrently with water until sulfate free. The column is then eluted at a flow rate of about 1 gal/ft$^3$min. with 0.1N sodium hydroxide (0.4% w/w). Elution is monitored with a recording pH controller and amino acids are collected to pH 12.0 to maximize arginine recovery. Fifty-four equivalents of the sodium hydroxide solution are necessary to elute the amino acids from each cubic foot of C-20 resin. The final concentration of amino acids is between about 0.85 and 1.0% w/w with no cation other than sodium present.

Recovery exceeds 95% of the amino acids loaded with losses equally distributed across the amino acid profile.

EXAMPLE 6

Concentration

The amino acid eluate from the previous step is reacidified to pH 3.0 with 1.5N sulfuric acid (5 ml/liter of solution). The amino acids are then loaded on a column identical to the one used for deionization.

After loading the amino acids are washed sulfate free with water, then eluted with 0.5N sodium hydroxide (2% w/w). Elution again requires 54 equivalents of sodium hydroxide per cubic foot of resin. Amino acids are collected to pH 11.5 to afford a solution containing between about 2.9 and 4% w/w amino acids.

EXAMPLE 7

Sterilization

A 3% solution of amino acids (pH 8.7) is steam injected at 280° F (holding time, 11 seconds) and then flashed into an evacuated chamber (124° F). This cycle is repeated five times. The residual ammonia after the five steam injection-flash evaporation sequences is approximately 50 ppm (0.005%).

EXAMPLE 8

The final colorless amino acid solution prepared by the above process has an amino acid content between about 2.9 and 4% w/w.

| Specifications | |
|---|---|
| Theoretical amino acid profile | Relative % of total protein |
| Aspartic acid | 10.4 |
| Threonine | 4.1 |
| Serine | 3.3 |
| Glutamic Acid | 7.7 |
| Proline | 3.4 |
| Cysteine | 0.3 |
| Glycine | 3.8 |
| Alanine | 8.4 |
| Valine | 9.6 |
| Methionine | 1.5 |
| Isoleucine | 0.3 |
| Leucine | 13.4 |
| Tyrosine | 2.4 |
| Phenylalanine | 8.0 |
| Lysine | 10.3 |
| Histidine | 7.2 |
| Arginine | 3.6 |

| Chemical Specifications | Quantity (based on dry weight amino acids) | |
|---|---|---|
| Chloride | $\leq$ 0.02 | % |
| Ammonia | $\leq$ 0.02 | % |
| Sulfate | $\leq$ 0.03 | % |
| Heavy metals (Pb,Zn,Cu,Mn) | $\leq$ 10.0 | ppm |
| Iron | $\leq$ 30 | ppm |
| Na | $\leq$ 1.6 | % |

We claim as our invention:

1. A process for the preparation of a nutritionally acceptable amino acid mixture suitable for intravenous administration which comprises the steps of:

a. heating erythrocytes to denature protein contained therein, followed by separation of the insoluble denatured protein formed thereby from the soluble components;

b. hydrolyzing the denatured protein from step (a) with sulfuric acid at a temperature equal to or greater than 200° F to afford a crude amino acid mixture essentially free of peptides, followed by partial neutralization with calcium hydroxide to a final pH of between 2.7 and 3.5, thereby affording a mixture of soluble amino acids and a cake comprising calcium sulfate and humin impurities;

c. desludging the mixture formed in step (b) by separating the amino acid solution from the calcium sulfate-humin cake;

d. decolorizing the amino acid solution obtained from step (c);

e. deionizing the decolorized amino acid solution from step (d) to remove nutritionally objectionable ions by loading the amino acid solution on a column of a strong cationic exchange resin comprising a sulfonated copolymer of styrene cross-linked with approximately 8% divinyl benzene and eluting the amino acids therefrom with dilute sodium hydroxide solution;

f. concentration of the amino acid solution obtained from step (e) by removal of water to afford an amino acid solution containing greater than 2% w/w of amino acids; and g. sterilization of the amino acid solution obtained from step (f) to remove microbial contamination.

2. The process of claim 1 wherein the erythrocytes used are bovine erythrocytes.

3. The process of claim 1 wherein, in step (b), the acid hydrolysis is effected by means of 8N sulfuric acid at a temperature 258° F or greater.

4. The process of claim 1 wherein, in step (d), decolorization is accomplished by means of activated charcoal.

5. The process of claim 8 wherein the activated charcoal is utilized in a ratio of from about 1 to 2% w/w relative to amino acid solution.

6. The process of claim 1 wherein, in step (d), decolorization is accomplished by passage of the hydrolysate from step (c) through a column of a strong cationic exchange resin of the type used in step (e) followed by passage through a column of a weak anionic macroreticular phenolformaldehyde resin.

7. The process of claim 1 wherein, in step (e), the cationic exchange resin is 40–80 mesh.

8. The process of claim 1 wherein, in step (e), the ion exchange column is washed sulfate-free with water after loading with amino acids.

9. The process of claim 1 wherein, in step (e), the sodium hydroxide solution used for elution is $\leq 0.1N$.

10. The process of claim 1 wherein, in step (f), the concentration is effected by loading the amino acid solution obtained from step (e) on a cationic exchange column of the type utilized in step (e), and eluting with sodium hydroxide solution of higher concentration than that utilized in step (e).

11. The process of claim 10 wherein the sodium hydroxide solution used for elution is approximately 0.5N.

12. The process of claim 10 wherein, prior to elution, the column is washed sulfate-free with water.

13. The process of claim 1 wherein, in step (g), residual volatiles are substantially removed during the sterilization process.

14. The process of claim 13 wherein sterilization and removal of residual volatiles are accomplished by means of steam injection-flash evaporation.

15. The process of claim 1 wherein the amino acid solution produced contains between about 2 and 4% w/w amino acids.

16. The process of claim 1 wherein the amino acid solution produced has an ammonia content of $\leq 0.02\%$.

17. The process of claim 1 wherein the amino acid solution produced is additionally spray dried to afford a dried mixture of crystalline amino acids.

* * * * *